(12) United States Patent
Frings et al.

(10) Patent No.: US 7,371,881 B2  
(45) Date of Patent: May 13, 2008

(54) PROCESS FOR THE PREPARATION OF ORGANOSILICON COMPOUNDS

(75) Inventors: Albert Frings, Brühl (DE); Louis Janssens, Merksem (BE); Stefan Lotter, Hanau (DE); Ulrich Deschler, Sailauf (DE); Alfred Alig, Geiselbach-Omersbach (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/497,633

(22) Filed: Aug. 2, 2006

(65) Prior Publication Data

US 2007/0066841 A1 Mar. 22, 2007

(30) Foreign Application Priority Data

Aug. 10, 2005 (DE) ............... 10 2005 037 690

(51) Int. Cl.  
*C07F 7/08* (2006.01)

(52) U.S. Cl. ................................... 556/427

(58) Field of Classification Search ............... 556/427  
See application file for complete search history.

(56) References Cited

U.S. PATENT DOCUMENTS

| | | | |
|---|---|---|---|
| 5,405,985 A | 4/1995 | Parker et al. | |
| 5,468,893 A | 11/1995 | Parker et al. | |
| 5,583,245 A | 12/1996 | Parker et al. | |
| 5,663,396 A | 9/1997 | Musleve et al. | |
| 6,384,255 B1 | 5/2002 | Backer et al. | |
| 6,384,256 B1 | 5/2002 | Backer et al. | |
| 6,423,859 B1 * | 7/2002 | Alig et al. | 556/427 |
| 6,448,426 B1 | 9/2002 | Backer et al. | |
| 6,777,569 B1 | 8/2004 | Westmeyer et al. | |

FOREIGN PATENT DOCUMENTS

| | | |
|---|---|---|
| DE | 2 141 159 | 1/1973 |
| EP | 0 694 552 A2 | 1/1996 |
| EP | 0 848 006 A2 | 6/1998 |
| EP | 1 130 023 A2 | 9/2001 |
| WO | WO 03/002573 A2 | 1/2003 |
| WO | WO 03/002576 A1 | 1/2003 |
| WO | WO 03/002577 A1 | 1/2003 |
| WO | WO 03/002578 A1 | 1/2003 |
| WO | WO 2004/043969 A1 | 5/2004 |

* cited by examiner

*Primary Examiner*—Samuel A Barts  
(74) *Attorney, Agent, or Firm*—Robert G. Weilacher; Smith, Gambrell & Russell

(57) ABSTRACT

A process for the preparation of an organosilicon compound of the formula (I)

$$(R^1R^2R^3SiR^4)_2S_x \qquad (I)$$

by reacting haloalkoxysilanes of the general formula (II)

$$R^1R^2R^3SiR^4X \qquad (II)$$

with a dry polysulphide of the general formula (III)

$$M_2S_z \qquad (III)$$

and/or dry sulphide of the general formula IV $$M_2S \qquad (IV)$$

and optionally sulphur in an organic solvent, the organic solvent being removed from the resulting suspension, the mixture containing the organosilicon compound of the general formula (I) and the solid MX being mixed with water containing at least one buffer, and the resulting phases being separated.

2 Claims, No Drawings

PROCESS FOR THE PREPARATION OF ORGANOSILICON COMPOUNDS

REFERENCE TO A RELATED APPLICATION

This application claims the benefit of German priority application No. 102005037690.8 filed Aug. 10, 2005, which is relied on herein.

INTRODUCTION AND BACKGROUND

The invention relates to a process for the preparation of organosilicon compounds.

It is known that silylalkylpolysulphanes can be prepared substantially by a nucleophilic substitution on chloroalkylsilanes with anionic polysulphides prepared in various ways (German Patent DE-PS 2141159). The working-up of the mixture consisting of the organosilicon compounds and of the solid formed in the nucleophilic substitution, in the present case a salt, is effected by filtration or centrifuging. The resulting salt is very finely divided if it is precipitated from an organic phase.

Furthermore, U.S. Pat. No. 6,777,569 discloses a process for the preparation of blocked mercaptosilanes, the metal salt of an organosilicon compound containing a mercapto group being reacted with an acyl halide in the presence of toluene. The working-up of the mixture consisting of the organosilicon compound and of the salt formed in the nucleophilic substitution is effected by complete dissolution of the salt in demineralized water and subsequent phase separation. The phase separation is decisively supported by the presence of toluene. In addition to the organosilicon compound, the organic phase therefore contains toluene, which has to be removed by distillation after the phase separation.

U.S. Pat. Nos. 5,405,985, 5,468,893, 5,663,396, 5,583,245 and EP-A 0694552 disclose processes which prepare the corresponding polysulphide in aqueous solution from sulphides and sulphur and react them in a two-phase system with haloalkylsilanes in the presence of toluene and a phase-transfer catalyst to give polysulphanes. In this procedure, the working-up of the mixture consisting of the organosilicon compound and of the salt formed in the nucleophilic substitution is effected by complete dissolution of the salt in demineralized water and subsequent phase separation. The phase separation is decisively supported by the presence of toluene. In addition to the organosilicon compound, the organic phase therefore contains toluene, which has to be removed by distillation after the phase separation. In this procedure, the phase-transfer catalyst or its degradation product remains in the sulphur-containing organosilicon compounds with a so far unexplained influence on the performance characteristics of the bis(silylalkyl)polysulphanes.

Furthermore, U.S. Pat. Nos. 6,448,426, 6,384,255, 6,384,256, WO 03/002573, WO 03/002576, WO 03/002577, WO 03/002578 and WO 04/043969 disclose processes which prepare the corresponding polysulphide in aqueous solution from sulphides and sulphur or hydrogen sulphides, alkali metal hydroxides and sulphur and react them in a two-phase system with haloalkylsilanes in the presence of a phase-transfer catalyst to give polysulphanes. The working-up of the mixture consisting of the organosilicon compound and of the salt formed in the nucleophilic substitution is effected by complete dissolution of the salt in water and subsequent phase separation. In this procedure, the phase-transfer catalyst or its degradation products remain in the sulphur-containing organosilicon compounds with a so far unexplained influence on the performance characteristics of the bis(silylalkyl)polysulphanes.

A disadvantage of the known processes in which the organosilicon compounds are prepared under anhydrous conditions is the difficult and expensive removal of the finely divided solids forming.

It is an object of the invention to provide a process which makes it possible to work up mixtures consisting of organosilicon compounds and solids in a manner which is as simple and economical as possible.

A further disadvantage of the known processes in which the polysulphanes are obtained by reacting the corresponding polysulphide, which is obtained in aqueous solution from sulphides and sulphur, in a two-phase system with haloalkylsilanes in the presence of a solvent, such as, for example, toluene, is that the sulphur-containing organosilicon compounds have to be freed from the solvent, for example by vacuum distillation. Another disadvantage is that the solvent obtained optionally has to be dried before further use.

A further object of the invention is to provide a process that permits the preparation of sulphur-containing organosilicon compounds which require no solvent for supporting the phase separation.

A further disadvantage of the known processes in which the polysulphanes are obtained by reacting the corresponding polysulphide, which is obtained in aqueous solution from sulphides and sulphur, in a two-phase system with haloalkylsilanes in the presence of a phase-transfer catalyst is that the sulphur-containing organosilicon compounds are contaminated with the phase-transfer catalyst or its degradation products.

A further object of the invention is to provide a process that permits the preparation of sulphur-containing organosilicon compounds which are free from a phase-transfer catalyst essential to the process or its degradation products.

SUMMARY OF THE INVENTION

The invention relates to a process for the preparation of an organosilicon compound of the general formula (I), $$(R^1R^2R^3SiR^4)_2S_x \qquad (I)$$

in which the meanings are as follows $R^1$, $R^2$, $R^3$ are: identical to or different from one another and are branched or straight-chain alkyl groups, preferably having a chain length of 1-8 C atoms, branched or straight-chain alkoxy groups, preferably having a chain length of 1-20 C atoms, particularly preferably having a chain length of 1-4 or 12-18 C atoms, very particularly preferably methoxy or ethoxy, alkyl ether group, alkylpolyether group or aryl radicals, preferably phenyl, toluyl or benzyl, at least one of the groups $R^1$, $R^2$, $R^3$ being an alkoxy group, $R^4$ is: a branched or straight-chain, saturated or unsaturated aliphatic, aromatic or mixed aliphatic/aromatic divalent $C_1$-$C_{30}$—, preferably $C_1$-$C_{20}$—, particularly preferably $C_1$-$C_{10}$—, very particularly preferably $C_1$-$C_7$—, most particularly preferably $C_3$—, hydrocarbon group, which is optionally substituted by F—, $C_1$—, Br—, I—, HS—, $NH_2$—, or NHR', where R' is a branched or straight-chain monovalent alkyl or alkenyl group, an aryl group, an arylkyl group, an alkylether group, an alkylpolyether group, x is a number >1, preferably from 2 to 8, particularly preferably from 2 to 6, by reacting haloalkoxysilanes of the general formula(II), $$R^1R^2R^3SiR^4X \qquad (II)$$

in which $R^1$, $R^2$, $R^3$, $R^4$ have the meaning from formula (I) and X is a halogen atom, preferably Cl, Br or I, with a dry polysulphide of the general formula (III)

$$M_2S_z \qquad (III)$$

and/or dry sulphide of the general formula IV, $$M_2S \qquad (IV)$$

in which M represents an alkali metal cation, an ammonium cation or half an alkaline earth metal or zinc cation and z represents a number from 2 to 8, preferably from 2 to 6, and optionally sulphur in an organic solvent, which is characterized in that the organic solvent is removed from the resulting suspension, the mixture containing the organosilicon compound of the general formula (I) and the solid MX is mixed with water, containing at least one buffer, and the resulting phases are separated.

The process according to the invention can be carried out without a catalyst, in particular without a phase-transfer catalyst.

DETAILED DESCRIPTION OF INVENTION

The organosilicon compound of the general formula (I) may be a mixture of organosilicon compounds of the general formula (I) having different sulphur chain lengths x.

The organosilicon compound of the general formula (I) may preferably be bis(triethoxysilylpropyl)disulphane, bis(triethoxysilylpropyl)tetrasulphane, bis(methyldiethoxysilylpropyl)disulphane, bis(methyldiethoxysilylpropyl)tetrasulphane, bis(dimethylethoxysilylpropyl)disulphane or bis(dimethylethoxysilylpropyl)tetrasulphane.

The reactants haloalkoxysilanes according to formula (II) and the sulphides according to formula (III) and/or formula (IV) can be initially introduced together in a solvent or solvent mixture and reacted or one of the two reactants is metered as such or as a solution into the second reactant. The second reactant may likewise be present as the substance or as a solution. For carrying out the process according to the invention, it is not critical which of the two reactants is initially introduced and which is metered in.

In a preferred form of the invention both reactants, haloalkoxysilanes according to formula II and sulphides according to formula (III) and/or formula (IV), can be initially introduced in an organic solvent or solvent mixture and then reacted.

The organic solvent can be an inert organic solvent. The inorganic solvent can be ether, for example diethyl ether, diisopropyl ether, dibutyl ether, methyl tert-butyl ether, tetrahydrofuran, dioxane, dimethoxyethane and diethoxyethane, alcohols, for example methanol, ethanol, propanol and ethylene glycol, and aliphatic or aromatic hydrocarbons, for example pentane, hexane, heptane, petroleum ether, benzene, toluene and xylene. The organic solvent can be chosen so that undesired transesterifications at the silicon atom are ruled out. Preferred organic solvents can be alcohols, in a particularly preferred embodiment the alcohol used corresponding to that of the alkoxy group bonded in the alkoxysilyl radical. Ethanol can particularly preferably be used as the organic solvent if one of the groups $R^1$, $R^2$, $R^3$ in formula (I) corresponds to an ethoxy group.

The organic solvent can have a water content of $\leqq 1\%$ by weight, preferably $\leqq 0.5\%$ by weight, particularly preferably $\leqq 0.1\%$ by weight.

The reaction time is dependent on the reaction temperature. The higher the reaction temperature, the shorter is the time required for complete reaction of the haloalkoxysilanes according to formula (II) with the sulphides according to formula (III) and/or formula (IV). The reaction time can be from 1 to 8 h.

The dry polysulphide of the general formula (III) can have a water content of $\leqq 10\%$ by weight, preferably $\leqq 5\%$ by weight, particularly preferably $\leqq 2\%$ by weight, very particularly preferably $\leqq 1\%$ by weight.

The dry sulphide of the general formula (IV) can have a water content of $\leqq 10\%$ by weight, preferably $\leqq 5\%$ by weight, particularly preferably $\leqq 2\%$ by weight, very particularly preferably $\leqq 1\%$ by weight.

The organic solvent can be separated from the resulting suspension by distillation.

The buffer which keeps the buffer solution within a pH range optimum for the stability of the organosilicon compounds can be substantially varied with respect to type and concentration. Buffers used can be organic and inorganic acids and bases and salts thereof, preferably alkaline metal, alkaline earth metal or ammonium salts of carboxylic acids, phosphoric acid, sulphuric acid, C1-C6 organo-, mono- or polycarboxylic acids. Buffers used can be, for example, $NaHCO_3$, $Na_2CO_3$, ammonium carbonate, sodium borate, monosodium phosphate, disodium phosphate, trisodium phosphate, monopotassium phosphate, dipotassium phosphate, tripotassium phosphate, monosodium sulphate, disodium sulphate, sodium acetate, potassium acetate, ammonium acetate, calcium acetate, sodium formate, sodium sulphide, sodium hydrogen sulphide, ammonia, monoethylamine, diethylamine, triethylamine, monoethanolamine, diethanolamine, triethanolamine, pyridine and aniline. Combinations of these buffers or combinations of these buffers with other buffers, for example acids or bases, can also be used.

Preferred buffers can be trisodium phosphate ($Na_3PO_4$), ammonium hydroxide ($NH_4OH$) and particularly preferably sodium bicarbonate $NaHCO_3$, the sodium bicarbonate establishing a pH of 7.5±0.5, causing no adverse environmental effect and having a comparatively low price.

The buffer can be present in a concentration of from 0.1 to 80% by weight, preferably from 0.1 to 20% by weight, particularly preferably from 0.1 to 10% by weight, very particularly preferably from 0.1 to 5% by weight, in the water.

The resulting phases after the addition of the water containing the buffer can contain the solid in dissolved or crystalline form, depending, inter alia, on the amount of water, temperature and further conditions.

The water containing the buffer can be added in an amount of from 10 to 150% by weight, preferably from 50 to 71% by weight, based on the organosilicon compound, if the solid is to be quantitatively dissolved.

The water containing the buffer can be added in an amount of from 0.1 to 30% by weight, preferably from 1 to 4% by weight, based on the organosilicon compound, if the solid is to be filtered off or centrifuged after the finely crystalline solid is converted into coarse solid particles by addition of a little water containing the buffer.

The solid can be the salt MX obtained in the preparation of the organosilicon compound of the general formula (I), M and X having the abovementioned meaning.

The addition of the water containing the buffer can be carried out at a temperature of 0-100° C., preferably 20-80° C., particularly preferably 40-60° C.

The time required for complete dissolution of the solid is dependent on the temperature. The higher the temperature, the shorter may be the time required for complete dissolution of the solid. The addition of the water containing the buffer can be effected in less than 1 h, preferably less than ½ h, particularly preferably less than ⅓ h.

For changing the morphology of the finely crystalline solid into coarse solid particles by addition of a little water containing the buffer, the temperature during the metering and duration of the addition may not be critical.

The resulting phases after the addition of the water containing the buffer can be carried out in a reactor or another container in the course of a ¼ h to 3 h.

The resulting phases after the addition of the water containing the buffer can be separated by filtration, centrifuging or sedimentation (in the case of undissolved solid) and decanting or discharging of the phases into different containers(in the case of dissolved solid), depending on whether the solid is dissolved or not. A pressure filter can be used for the filtration.

The advantages of the process according to the invention is that it is possible to dispense with filters or centrifuges for separating off the solids, which constitutes an enormous technical simplification of the process for the preparation of organosilicon compounds and a reduction of the production costs, or the filtration or centrifuging after the change of the morphology of the solids can be substantially facilitated and the duration for this process step can be drastically shortened if it is preferred to separate off the coarse solid particles in solid form capable of being disposed of on a landfill. A further advantage, compared with the known processes which operate with a phase-transfer catalyst and therefore give organosilicon compounds contaminated with the phase-transfer catalyst or the degradation products of the phase-transfer catalyst is that no impurities of this type are present in the organosilicon compounds. Compared with the known processes, which use organic solvents, such as, for example, toluene, for improving the phase separation, the process presented has the advantage that no organic solvents are required for supporting the phase separation and working-up, for example drying thereof, is dispensed with.

EXAMPLES

Example 1

2535 g of ClPTES (3-chloropropyltriethoxysilane) are reacted with 870 g of NPS (sodium polysulphide, $Na_2S_z$ where z on average is 4, water content 0.1% by weight) in 2165 ml of ethanol at 78° C. Ethanol is removed by distillation from the reaction mixture obtained on a rotary evaporator, finally at a bottom temperature of 100° C. and a pressure of <1 mbar. The ethanol concentration at the end of the distillation is <0.1% by weight. A total of 1800 g of buffer solution (2%) of $NaHCO_3$ in demineralized water) are metered at 50° C. through a dip tube into the mixture of 3378 g of bis(triethoxysilylpropyl)tetrasulphane and NaCl obtained in this manner (theoretical composition: 2769 g of bis(triethoxysilylpropyl)tetrasulphane and 609 g of NaCl), in order to dissolve the salt. After addition of about half the buffer solution, the stirrer is set to the lowest possible speed. Two phases immediately form. All of the salt is present in the aqueous phase. The phase separation persists to the end of the addition of the buffer solution, owing to the low stirrer speed. During the addition of the buffer solution, the appearance of the NaCl changes. The finely crystalline salt as obtained in the synthesis of bis(triethoxysilylpropyl)tetrasulphane from NPS and ClPTES becomes increasingly more coarsely crystalline. At the end of the metering, when the major part of NaCl has dissolved, the salt becomes finely crystalline again. Flocculation is observed in the aqueous phase after the salt has dissolved. As long as undissolved salt is present in the aqueous phase, the supernatant yellow solution is clear. Flocs are not detectable.

The entire batch is discharged from the reactor and weighed:

The amount used is 5178 g. The weight of product is 5135 g. 43 g remain in the reactor.

During the discharge, the aqueous phase and organic phase are separated:

The amount of aqueous phase is 2255 g (2409 g are theoretically expected). The amount of organic phase is 2880 g (2769 g are theoretically expected). The intermediate phase is added to the organic phase.

193 g of intermediate phase in which a relatively large amount of water in addition to product is present are separated off in a separating funnel. Organic phase and intermediate phase are dried on a rotary evaporator at 100° C. and a pressure of <1 mbar.

After drying of the organic phase, 2601 g of bis(triethoxysilylpropyl)tetrasulphane are obtained (25 g of water and 29 g of NaCl are separated off).

After drying of the intermediate phase, a further 108 g of bis(triethoxysilylpropyl)tetrasulphane are obtained (61 g of water and 13.6 g of NaCl are separated off).

Altogether, 2709 g of bis(triethoxysilylpropyl) tetrasulphane are isolated; this corresponds to 97.8% of the theoretically expected amount of 2769 g of product. If losses during the experimental procedure and variations in the composition of the reaction mixture are taken into account, it may be assumed that the product is obtained quantitatively.

The flocs in the aqueous phase gradually settle. The supernatant yellow solution becomes clear.

Example 2

700 g of ClPTES (3-chloropropyltriethoxysilane) are reacted with 239 g of NPS (sodium polysulphide, $Na_2S_z$ where z is on average 4, water content 0.1% by weight) in 595 ml of ethanol at 78° C. Ethanol is removed by distillation from the reaction mixture obtained on a rotary evaporator, finally at a bottom temperature of 100° C. and a pressure of <1 mbar. The ethanol concentration at the end of the distillation is <0.1% by weight. Only 30 ml of buffer solution are metered at 50° C. through a dip tube into the mixture of 928 g of bis(triethoxysilylpropyl)tetrasulphane and NaCl obtained in this manner (theoretical composition: 761 g of bis(triethoxysilylpropyl)tetrasulphane and 167 g of NaCl). The finely crystalline salt becomes coarsely crystalline and can then be very easily filtered off. The filtrate has a yellow colour. No formation of two liquid phases takes place since the amount of buffer solution, in contrast to Example 1, is not sufficient to dissolve the salt (formation of a solid and a liquid phase).

220 g of moist salt (NaCl) and 716 g of bis(triethoxysilylpropyl)tetrasulphane are isolated.

The salt is dissolved in 400 g of buffer solution. Two phases form, the appearance of the organic phase corresponding to the intermediate phase usually occurring. The phases are separated and the organic phase is dried on a rotary evaporator. 29 g of product are isolated (30 g of water and 14.5 g of NaCl are separated off). A total of 745 g of Si69 are isolated; this corresponds to 97.9% of the theoretically expected amount of 761 g of product.

Example 3

2580 g of ClPTES (3-chloropropyltriethoxysilane) are reacted with 304 g of NPS (sodium polysulphide, Na2Sz where z is on average 4, water content 0.1% by weight) and 298 g of NST (dry sodium sulphide, $Na_2S$, water content <1% by weight) in 2340 ml of ethanol at 78° C. Ethanol is removed by distillation from the reaction mixture obtained on a rotary evaporator, finally at a bottom temperature of 100° C. and a pressure of <1 mbar. The ethanol concentration at the end of the distillation is <0.1% by weight. A total of 1840 g of buffer solution (2% of $NaHCO_3$ in demineralized water) is metered at 50° C. through a dip tube into the mixture of 3201 g of bis(triethoxysilylpropyl)disulphane and NaCl obtained in this manner (theoretical composition: 2602 g of bis(triethoxysilylpropyl)disulphane and 599 g of NaCl), in order to dissolve the salt. During the addition of the buffer solution, it is observed that the salt initially forms increasingly large aggregates. The salt takes up ⅓ of the water without an aqueous phase being detectable. The salt aggregates become so large that they immediately settle when the stirrer is switched off.

After addition of the total amount of buffer solution and phase separation, the following are isolated:

2371 g of aqueous phase (red-brown colour; stronger H2S odour in comparison with the aqueous phase from the working-up of the mixtures from Example 1), 119 g of intermediate phase (typical appearance), 2516 g of organic phase.

2439 g of aqueous phase are expected (amount of salt plus buffer solution). The aqueous phase has a pH of 8. The COD (chemical oxygen demand, determination according to DIN 38409 Part 41), is 44 905 mg/kg and therefore very high in comparison with the aqueous phase from the working-up of the mixture of bis(triethoxysilylpropyl)tetrasulphane and NaCl (Example 1). This extremely high COD is due to the $Na_2S$ which is used in excess in the synthesis of bis (triethoxysilylpropyl)disulphane and dissolves in the aqueous phase. The strong H2S odour can also be explained therewith.

After working-up of the organic phase (removal of the water on a rotary evaporator at 100° C. and a pressure of <1 mbar and filtration), 2455 g of product having the pale yellow colour typical of bis(triethoxysilylpropyl)disulphane are obtained. 37 g of water and 3.3 g of filter residue (salt) are separated off.

A further 37 g of product are obtained from the intermediate phase. The difference compared with the 119 g of intermediate phase isolated is accounted for by water and salt. Altogether 2492 g of Si266 are isolated (corresponds to 95.7% of the calculated amount).

The invention claimed is:

1. Process for the preparation of an organosilicon compound of the formula (I)

$$R^1R^2R^3SiR^4)_2S_x \quad (I)$$

in which the meanings are as follows $R^1$, $R^2$, $R^3$ are: identical to or different from one another and are branched or straight-chain alkyl groups, branched or straight-chain alkoxy groups or aryl radicals, at least one of the groups $R^1$, $R^2$, $R^3$ being an alkoxy group, $R^4$ is: a branched or straight-chain, saturated or unsaturated, aliphatic, aromatic or mixed aliphatic/aromatic divalent $C_1$-$C_{30}$ hydrocarbon group, x is a number >1, comprising reacting, without a phase-transfer catalyst, haloalkoxysilanes of the general formula (II)

$$R^1R^2R^3SiR^4X \quad (II)$$

in which $R^1$, $R^2$, $R^3$, $R^4$ have the above meaning from formula (I) and

X is a halogen atom, with a dry polysulphide of the formula (III)

$$M_2S_z \quad (III)$$

and/or dry sulphide of the general formula IV $$M_2S \quad (IV)$$

in which

M represents an alkali metal cation, an ammonium cation or half an alkaline earth metal or zinc cation and z represents a number from 2 to 8, and optionally sulphur, in an organic solvent, to form a suspension, removing the organic solvent from the suspension, obtaining a mixture containing the organosilicon compound of the formula (I) and the solid MX and mixing said mixture with water, containing at least one buffer in an amount of from 0.1 to 80% by weight in the water to form a plurality of phases.

2. The process according to claim 1 further comprising separating the phases.

* * * * *

UNITED STATES PATENT AND TRADEMARK OFFICE
CERTIFICATE OF CORRECTION

PATENT NO. : 7,371,881 B2
APPLICATION NO. : 11/497633
DATED : May 13, 2008
INVENTOR(S) : Albert Frings et al.

It is certified that error appears in the above-identified patent and that said Letters Patent is hereby corrected as shown below:

Col. 8 lines 9-10

In Claim 1, Formula (I) should read as follows:

$$(R^1R^2R^3SiR^4)_2S_x$$

Signed and Sealed this

Fifth Day of August, 2008

JON W. DUDAS
*Director of the United States Patent and Trademark Office*